United States Patent [19]

Markham

[11] Patent Number: 5,176,699
[45] Date of Patent: Jan. 5, 1993

[54] SURGICAL DEVICE WITH DOUBLE JAW ACTUATION

[76] Inventor: Harold Markham, 508 N. Rexford Dr., Beverly Hills, Calif. 90210

[21] Appl. No.: 710,402

[22] Filed: Jun. 5, 1991

[51] Int. Cl.⁵ .............................................. A61B 17/28
[52] U.S. Cl. .................................. 606/206; 606/207; 606/208
[58] Field of Search .................... 606/205–208, 606/174, 167, 170, 171; 128/751; 81/364, 342, 381, 393, 407, 413; 294/19.1, 115

[56] References Cited

U.S. PATENT DOCUMENTS

| | | | |
|---|---|---|---|
| 2,579,536 | 12/1951 | Barr | 294/19.1 X |
| 2,790,437 | 4/1957 | Moore | 128/751 |
| 3,328,066 | 6/1967 | Johnston | 294/115 X |
| 3,989,049 | 11/1976 | Yoon | 606/206 X |
| 4,122,856 | 10/1978 | Mosior et al. | 606/174 X |
| 4,243,047 | 1/1981 | Olsen | 128/751 |
| 4,646,751 | 3/1987 | Maslanka | 606/208 X |
| 4,763,669 | 8/1988 | Jaeger | 128/751 |
| 4,887,612 | 12/1989 | Esser et al. | 606/208 X |
| 4,944,093 | 7/1990 | Falk | 606/174 X |
| 4,961,430 | 10/1990 | Sheahon | 606/171 X |

FOREIGN PATENT DOCUMENTS

| | | | |
|---|---|---|---|
| 980703 | 12/1982 | U.S.S.R. | 606/174 |
| 2119696 | 11/1983 | United Kingdom | 606/208 |

*Primary Examiner*—Michael H. Thaler
*Attorney, Agent, or Firm*—Poms, Smith, Lande & Rose

[57] ABSTRACT

A surgical device having a pair of slidably interlocking spring biased upper and lower shaft members. A grasping handle is associated with one end of the interlocking shaft members for grasping the same and sliding the upper shaft member forwardly along the lower shaft member. A grasping jaw member is pivotally connected to the other end of the shaft members, the jaw members being in meshing engagement thereby effecting a double jaw opening and closing when the upper shaft member is actuated with respect to the lower shaft member.

14 Claims, 3 Drawing Sheets

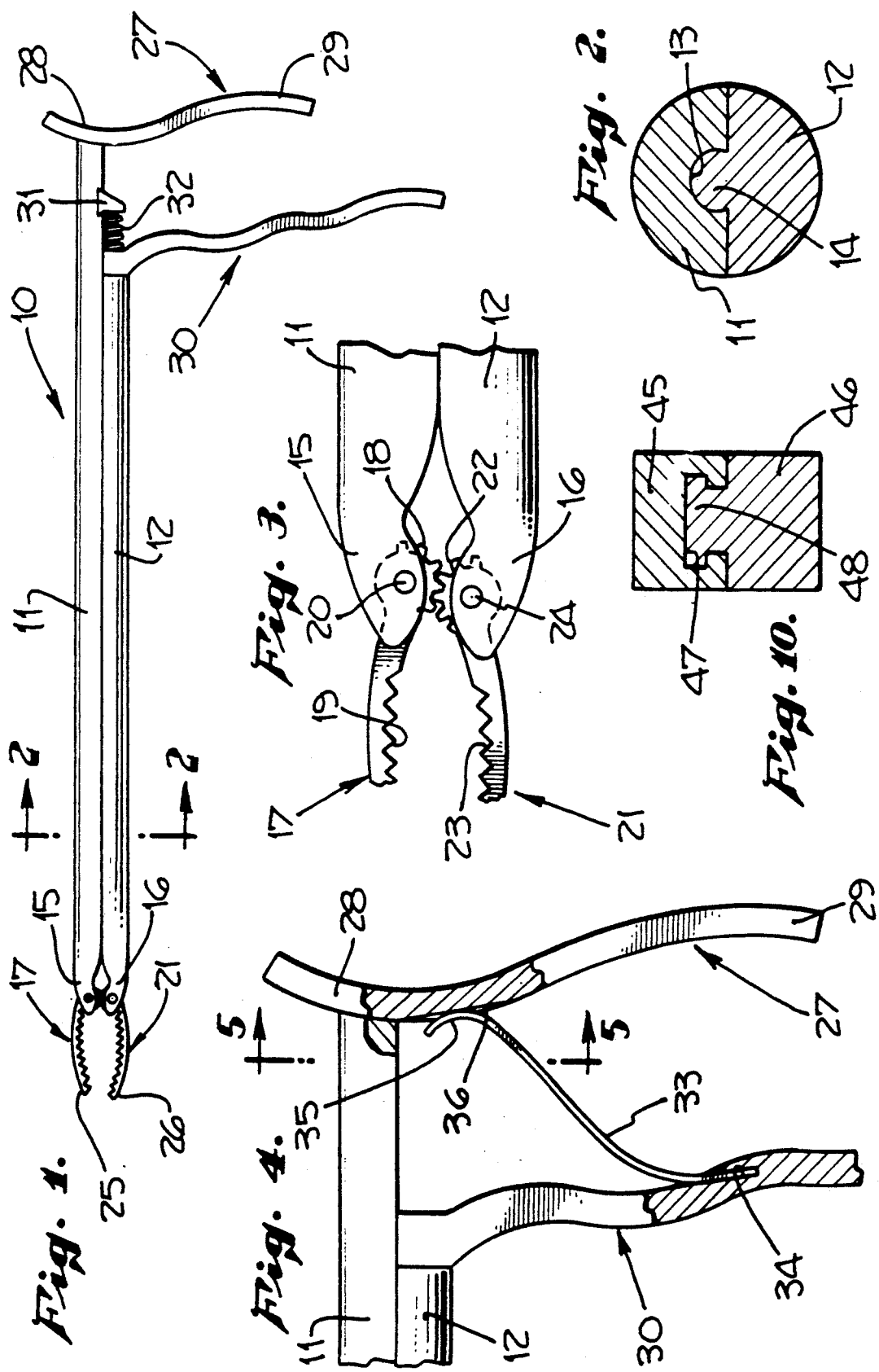

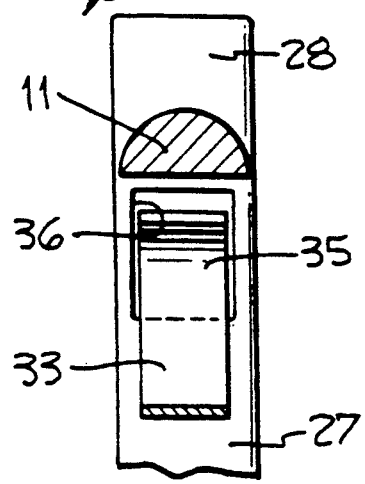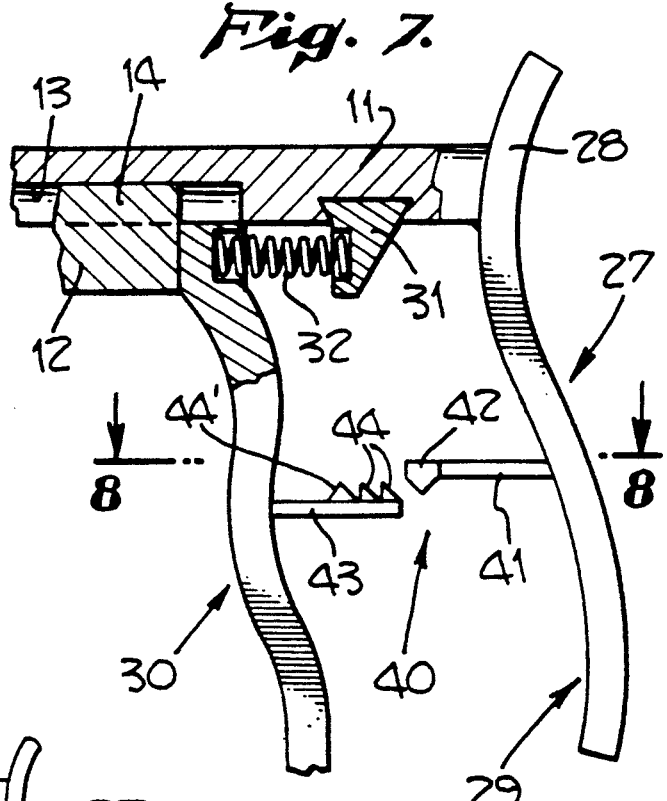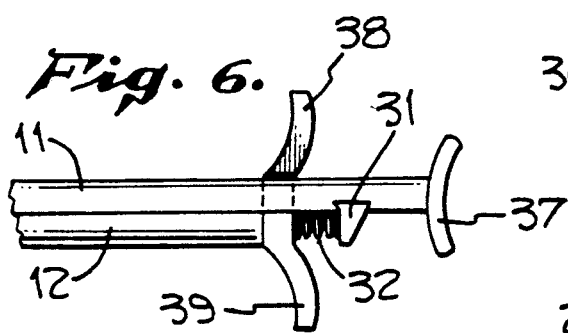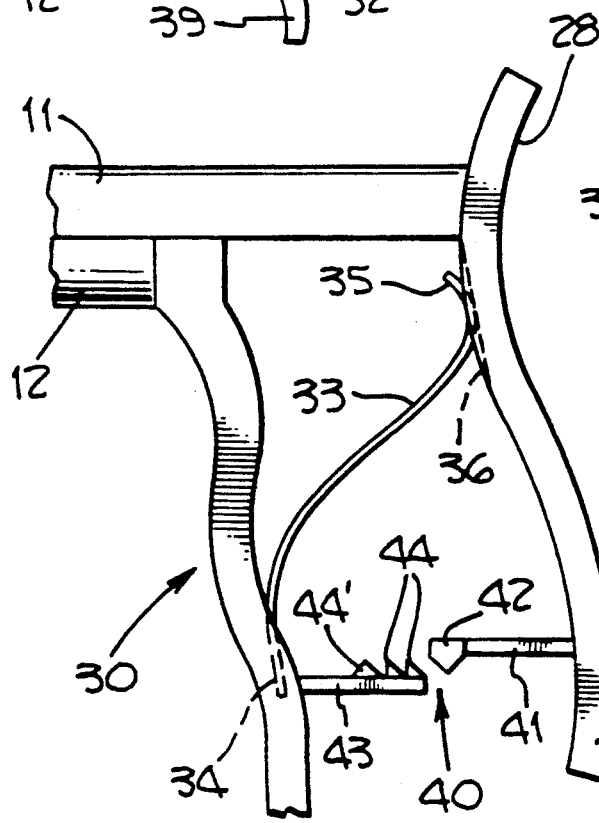

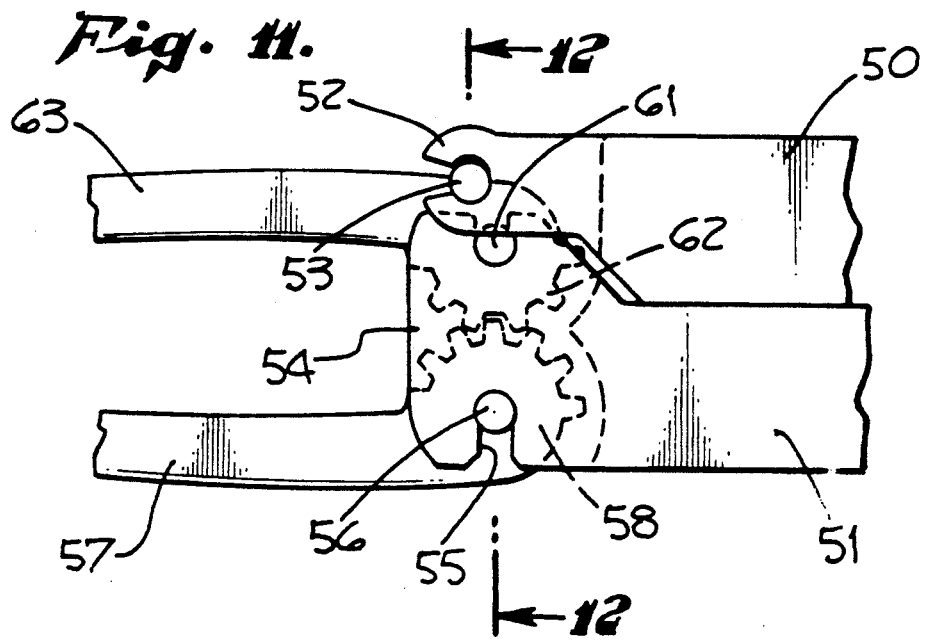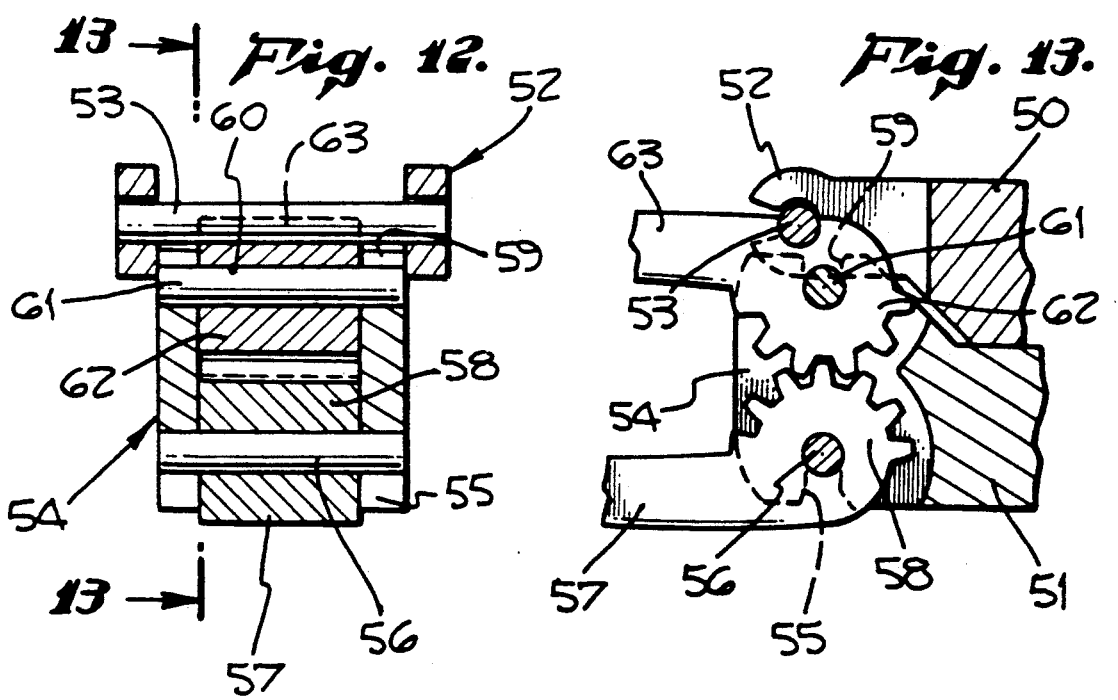

SURGICAL DEVICE WITH DOUBLE JAW ACTUATION

BACKGROUND OF THE INVENTION

1. Field of the Invention

The invention relates to surgical devices; and, more particularly, to a surgical tool having a pair of grasping jaws actuated to open and close.

2. Description of the Prior Art

In working inside of the abdominal cavity of a patient, the surgeon makes a hole in the patient's body and manipulates a surgical instrument that is passed through an elongated small diameter hollow tube or cannula inserted into the hole in the patient's abdominal cavity. Such a cannula may have an outer diameter as small as eleven millimeters and be about 8 to 9" long. The surgeon views the interior of the abdominal cavity through a conventional lens system associated with the patient which projects the interior view on a video screen. Such an instrument should be able to be inserted through such a small diameter tube, grasp or separate tissue, coagulate tissue, etc. Such an instrument should be about 12 to 14" long and should allow the surgeon to grasp with ease. The jaws of such an instrument should be able to open and close outside of the cannula with the parts of the instruments effecting such opening and closing working within the cannula.

SUMMARY OF THE INVENTION

It is an object of this invention to provide a surgical device having a double jaw opening and closing action.

It is a further object of this invention to provide such a device having a spring biasing a pair of interlocking elongated members, one of the members having a grasping jaw at one end meshing with a like grasping jaw at one end of the other of the members.

These and other objects are preferably accomplished by providing a surgical device having a pair of slidably interlocking spring biased upper and lower shaft members. A grasping handle is associated with one end of the interlocking shaft members for grasping the same and sliding the upper shaft member forwardly along the lower shaft member. A grasping jaw member is pivotally connected to the other end of the shaft members, the jaw members being in meshing engagement thereby effecting a double jaw opening and closing when the upper shaft member is actuated with respect to the lower shaft member.

BRIEF DESCRIPTION OF THE DRAWING

FIG. 1 is a vertical view of a surgical device in accordance with the teachings of the invention;

FIG. 2 is a view taken along lines 2—2 of FIG. 1;

FIG. 3 is a detailed view of a portion of the device of FIG. 1;

FIG. 4 is a view similar to FIG. 1 showing a modification of the device of FIG. 1;

FIG. 5 is a view taken along lines 5—5 of FIG. 4;

FIG. 6 is a vertical view of a portion of the apparatus of FIG. 1 showing a modification of the handle portions thereof;

FIG. 7 is a vertical view of a portion of the apparatus of FIG. 1 showing a modification thereof;

FIG. 8 is a view taken along lines 8—8 of FIG. 7;

FIG. 9 is a view similar to FIG. 4 adding the ratchet mechanism of FIGS. 7 and 8 thereto;

FIG. 10 is a view similar to FIG. 2 showing a modification of the interlocking means thereof;

FIG. 11 is a view similar to FIG. 3 showing another modification of the grasping means;

FIG. 12 is a view taken along lines 12—12 of FIG. 11; and

FIG. 13 is a view taken along lines 13—13 of FIG. 12.

DESCRIPTION OF THE PREFERRED EMBODIMENT

Referring now to FIG. 1 of the drawing, a surgical device 10 is shown having a pair of upper and lower elongated shaft members 11, 12. As seen in FIG. 2, upper shaft member 11 is generally round in shape with an elongated rounded cavity 13 extending therealong. Lower shaft member 12 is also generally round in shape with an elongated rounded protrusion 14 configured similarly to cavity 13 and adapted to ride therein.

Shaft member 11 terminates at its forward end in a tapered end 15 (FIG. 3). Shaft member 12 terminates at its forward end in a tapered end 16. A first upper jaw member 17, having a gear 18 at one end and a plurality of spaced teeth 19 extending therefrom is pivotally connected to end 15 by pivot pin 20. In like manner, a second lower jaw member 21, having a gear 22 at one end and a plurality of spaced teeth 23 extending therefrom is pivotally connected to end 16 by a pivot pin 24. As seen in FIG. 1, teeth 19, 23 face inwardly toward each other and each set of teeth 19, 23 curve to a terminal end, such as ends 25, 26, respectively.

Upper shaft member 11 terminates at the rear in a contoured gripping member or first handle portion 27 having shaft member 11 fixed thereto. Handle portion 27 is curved at top end 28 to provide a palm rest for the surgeon, the integral lower inwardly curved end 29 providing a palm rest.

Lower shaft portion 12 has at its rear end a second handle portion 30 having shaft portion 12 fixed thereto at its upper end. Handle portion 30 is contoured to receive therearound the fingers of the surgeon.

A stop member 31 may be provided on the underside of upper shaft member 11. A coiled spring 32 is fixed at one end of the upper end of handle portion 30 and at its other end to stop member 31 (of course, coiled spring 32 need not be fixed to either handle portion 30 or stop member 31 but is disposed therebetween in any suitable manner). Spring 32 thus normally biases first handle portion 27 away from second handle portion 30.

In operation, the surgeon grasps handle portions 27, 30 with his or her fingers about handle portion 30, his or her palm against parts 28 and 29 of handle portion 27. The surgeon squeezes handle portions 27, 30 together against the bias of spring 32. This moves upper shaft portion 11, keyed to lower shaft portion 12 by cavity 13 and protrusion 14, along lower shaft portion 12 in a straight aligned manner. The forward stroke of the surgeon's palm is short driving upper shaft member 11 forward with upper gear 18 meshing with lower gear 22 to close the hinged jaw members 17, 21. That is, as the two gears 18, 22 mesh on the forward movement of upper shaft member 11, lower jaw member 21 moving clockwise bringing end 26 upwardly. A double jaw opening and closing action is thus effected.

As an alternative to spring 32 and stop member 31, as seen in FIG. 4, wherein like numerals refer to like parts of the device of FIGS. 1 and 2, a short flat spring 33 is fixed at one end 34 to handle portion 30 and extends to and curves adjacent handle portion 27 at curved end 35.

As seen in FIG. 5, curved end 35 abuts against and is disposed in a notch 36 on handle portion 27 thereby retaining the same in position. Thus, spring 33 biases handle portions 27, 30 apart. When they are squeezed by the surgeon, as heretofore discussed, upper shaft member 11 moves forward along lower shaft member 12 as heretofore discussed. When released, handle portions return to the FIG. 4 position.

Another embodiment of the handle portions are shown in FIG. 6 wherein like numerals refer to like parts of the embodiment of FIG. 1. Here, handle portion 37, fixed to upper shaft member 11, is a curved member providing a thumb rest for the surgeon. Handle portions 38, 39, fixed to upper and lower shaft members 12, respectively, are arcuate members to provide engagement by the forefinger (upper handle portion 38) and middle and fourth finger (lower handle portion 39) of the surgeon.

As seen in FIG. 7, a ratchet mechanism 40 may be added to the embodiment of FIGS. 1 and 4 to assist in operation of the devices of FIGS. 1 and 4. This provides firm stable operation of the devices of FIGS. 1 and 4. Thus, referring to FIG. 7 wherein like numerals refer to like parts of the embodiment of FIG. 1, an elongated member 41 is fixed to handle portion 29 and extends toward handle portion 30 terminating in a single downwardly extending tapered tooth 42 (see also FIG. 8). A like elongated member 43 (FIG. 7) is fixed to and extends from handle portion 30 to handle portion 29. Member 43 terminates in a plurality of spaced upwardly extending tapered teeth 44 (see also FIG. 8). Members 41, 43 may be resilient and tooth 42 engages teeth 44 when handle portion 29, 30 are squeezed together. This provides firm stable actuation of device 10. When tooth 42 moves past the last tooth of teeth 44 (e.g., tooth 44'—FIG. 8), it drops downwardly and handle portion 29 returns to the FIG. 1 position. Thus, ratchet mechanism 40 provides an overriding ratchet means to hold jaw members 17, 21 closed.

As seen in FIG. 9, wherein like numerals refer to like parts of the embodiment of FIG. 4, the embodiment of FIG. 4 has been modified to add the ratchet mechanism 40 of the embodiment of FIGS. 7 and 8. Further description is deemed unnecessary.

The interengagement of shaft members 11, 12 can be accomplished in any suitable matter. For example, as seen in FIG. 10, instead of the knob or protrusion 14 and cavity 13 interengagement of FIG. 2, upper shaft member 45 may have a T-shaped slot 47 receiving therein a like configured T-shaped member 48 of lower shaft member 46. Other variations may occur to an artisan.

The shaft members 11, 12 or 45, 46 may be connected together for gripping in any suitable manner. Thus, as seen in FIGS. 11 to 13, shaft members 50, 51, otherwise identical to shaft members 12 of FIG. 1 and interconnected in like manner, are shown. Upper shaft member 50 terminates at the forward end in a rounded slotted yoke 52 (see also, FIG. 12) adapted to receive a pin 53 connected to jaw member 63 therein in a snap fitting relationship. Lower shaft member 51 terminates in a yoked head 54 having a first lower slot 55 receiving a pin 56 therein (FIG. 12) in a snap fitting relationship. Pin 56 is integral with lower jaw member 57 which may be otherwise similar to lower jaw member 21 with suitable teeth 23 thereon. Pin 56 also is the axle for toothed gear 58 (FIG. 13) having lower jaw member 57 integral therewith.

Head 54 also has a slot 59 at its upper end (FIG. 13) receiving in a rounded hole 60 therein a pin 61. Pin 61 is the axle for gear 62 having upper jaw member 63 integral therewith which is also otherwise similar to upper toothed jaw member 17.

The meshing of gears 58, 62 is identical to the meshing of gear 18, 22 and the operation of shaft members 45, 46 is also identical to the operation of device 10 of FIG. 1. Thus, further discussion is deemed unnecessary.

It can be seen that there is a new improved surgical device having upper and lower grasping jaws which are in meshing engagements providing an effective double jaw opening and closing action. The short stroke of shaft members 11, 12 thus only requires a short ratchet mechanism 40. The upper jaw member 17 actuates the lower jaw member 21.

I claim:

1. A surgical device comprising:
   a first upper rigid elongated shaft member keyed along a substantial portion of its length to a second lower rigid elongated shaft member for reciprocal movement therealong in parallel relation thereto;
   handle means at one end of said first and second shaft members for grasping said device;
   biasing means associated with said first and second shaft members for normally biasing said first shaft member in a direction laterally along said second shaft member;
   an upper jaw member;
   a lower jaw member;
   said upper jaw member being pivotally connected to said upper shaft member and said lower jaw member being pivotally connected to said lower shaft member, each of said jaw members having a plurality of spaced teeth thereon, the teeth of one of said jaw members facing the teeth of the other of said jaw members; and
   said jaw members being in meshing engagement whereby reciprocation of said upper shaft member in a direction sliding along said lower shaft member and toward said jaw members and parallel to said lower shaft member moves said upper jaw member in a counterclockwise direction whereby said lower jaw member, in meshing engagement with said upper jaw member, moves in a clockwise direction thereby moving the teeth of said jaw members together.

2. In the device of claim 1 wherein each of said jaw members taper to a point.

3. In the device of claim 2 wherein each of said jaw members are arcuate in cross section.

4. In the device of claim 1 wherein each of said jaw members has an integral gear portion pivotally connected to its respective shaft member, said gear portions having gear teeth thereon in meshing engagement.

5. In the device of claim 1 wherein said upper shaft member has a top wall and a bottom wall, and said handle means includes a handle portion fixedly secured to one end of said lower shaft member having an upper end and a downwardly extending lower end, said biasing means including a stop member mounted on the bottom wall of said upper shaft member, and a spring mounted between the upper end of said handle portion and said stop member.

6. In the device of claim 5 including a second handle portion fixed to one end of said upper shaft member and spaced from said first mentioned handle portion, each of said handle portions being contoured to fit the hand of a user.

7. In the device of claim 1 wherein said handle means includes a first handle portion fixedly secured to one end of said upper shaft member, and a second handle portion fixedly secured to one end of said lower shaft member and spaced from said first handle portion, said handle portions being contoured to fit the hand of a user.

8. In the device of claim 7 including a third handle portion being fixed to said lower shaft member extending upwardly therefrom, said first, second and third handle portions being arcuate in cross section with said first handle portion curving away from said second and third handle portions and adapted to be engaged by a thumb of a user, said second and third handle portions curving away from said first handle portion, said second handle portion being adapted to be engaged by a middle and fourth finger of a user and said third handle portion being adapted to be engaged by a forefinger of a user.

9. In the device of claim 1 wherein said first upper shaft member and said second lower shaft member are keyed to each other by an elongated cavity on one of said shaft members receiving therein a like configured interlocking member on the other of said shaft members.

10. In the device of claim 1 wherein said handle means includes a first handle portion fixed to one end of said upper shaft member and a second handle portion fixed to one end of said lower shaft member, said biasing means including a flat resilient spring fixed to said second handle portion and extending to and curving about said first handle portion forming a curved end abutting against said first handle portions.

11. In the device of claim 10 wherein said first handle portion includes a notch therein facing said second handle portion receiving said curved end therein.

12. In the device of claim including ratchet means associated with said handle means for ratcheting said upper shaft member with respect to said lower shaft member when said upper shaft member is reciprocated along said lower shaft member.

13. In the device of claim 12 wherein said handle means includes a first handle portion fixed to one end of said upper shaft member and a second handle portion fixed to one end of said lower shaft member and spaced from said first handle portion, said ratchet means including a first elongated ratchet member fixed to said first handle portion and extending toward said second handle portion, a second elongated ratchet member fixed to said second handle portion and extending toward said first handle portion, one of said ratchet members having at least one downwardly extending ratchet tooth thereon, the other of said ratchet members having a plurality of upwardly extending ratchet teeth thereon, said ratchet tooth being normally biased away from engagement with said ratchet teeth by said biasing means, said ratchet tooth being adapted to engage and ratchet into said ratchet teeth when said first and second handle portions are squeezed against the bias of said biasing means.

14. A surgical device comprising:
a first upper rigid elongated shaft member keyed along a substantial portion of its length to a second lower rigid elongated shaft member for reciprocal movement therealong in parallel relation thereto;
handle means at one end of said first and second shaft members for grasping said device;
biasing means associated with said first and second shaft members for normally biasing said first shaft member in a direction laterally along said second shaft member;
an upper jaw member;
a lower jaw member;
said upper jaw member being pivotally connected to said upper shaft member and to an extension portion of said lower shaft member, and said lower jaw member being pivotally connected only to said lower shaft member, each of said jaw members having a plurality of spaced teeth thereon, the teeth of one of said jaw members facing the teeth of the other of said jaw members; and
said jaw members being in meshing engagement whereby reciprocation of said first upper shaft member in a direction sliding along said lower shaft member and toward said jaw members and parallel thereto moves said upper jaw member in a counterclockwise direction whereby said lower jaw member, in meshing engagement with said upper jaw member, moves in a clockwise direction thereby moving the teeth of said jaw members together.

* * * * *